United States Patent [19]

Haacke

[11] Patent Number: 4,701,706

[45] Date of Patent: Oct. 20, 1987

[54] GENERALIZED RECONSTRUCTION TECHNIQUE

[75] Inventor: E. Mark Haacke, University Hts., Ohio

[73] Assignee: Picker International, Inc., Highland Hts., Ohio

[21] Appl. No.: 764,439

[22] Filed: Aug. 9, 1985

Related U.S. Application Data

[63] Continuation-in-part of Ser. No. 731,509, May 7, 1985.

[51] Int. Cl.$^4$ ............................................. G01R 33/20
[52] U.S. Cl. ...................................... 324/309; 324/307
[58] Field of Search ............... 324/300, 307, 309, 313; 358/111, 139; 128/653; 378/99; 364/200

[56] References Cited

U.S. PATENT DOCUMENTS

| | | | |
|---|---|---|---|
| 3,873,909 | 3/1975 | Ernst | 324/0.5 R |
| 3,916,385 | 10/1975 | Parmar et al. | 364/200 |
| 4,300,096 | 11/1981 | Harrison et al. | 324/309 |
| 4,321,537 | 3/1982 | Yokokawa et al. | 324/312 |
| 4,340,862 | 7/1982 | Percival et al. | 324/309 |
| 4,354,157 | 10/1982 | Feiner | 324/309 X |
| 4,355,282 | 10/1982 | Young | 324/309 |
| 4,384,255 | 5/1983 | Young et al. | 324/309 |
| 4,451,788 | 5/1984 | Edelstein et al. | 324/309 |
| 4,499,493 | 2/1985 | Nishimura | 358/111 |
| 4,506,327 | 3/1985 | Tam | 364/414 |
| 4,516,074 | 5/1985 | Sugimoto | 324/309 |
| 4,516,075 | 5/1985 | Moran | 324/309 |
| 4,516,261 | 5/1985 | Harding et al. | 382/6 |
| 4,591,789 | 5/1986 | Glover | 324/307 |
| 4,617,624 | 10/1986 | Goodman | 364/200 |

OTHER PUBLICATIONS

The Fourier Transform and Its Applications pp. 200–201.

*Primary Examiner*—Michael J. Tokar
*Attorney, Agent, or Firm*—Fay, Sharpe, Beall, Fagan, Minnich & McKee

[57] ABSTRACT

The resonance signals from a magnetic resonance imaging apparatus are discretely sampled. The sampled data are non-uniform in data space due to motion, eddy currents in the magnetic field, inaccurate timing in the application of the gradient magnetic fields, non-uniform sampling of the data, or the like. The discretely sampled data, $s(k_x, k_y)$, is mapped from data space to image space by a generalized transform. The generalized transform, unlike a Fourier transform, concurrently corrects for the non-uniformity as it transforms the non-uniform data space data into image space data with a preselected distribution, e.g. uniform. For a given y position of non-uniformly sampled data $s(k,y)$, the estimated spin density $\bar{\rho}(x,y)$ is related to the actual spin density $\rho(x,y)$ by the equation:

$$\bar{\rho}(x_u,y) = \frac{1}{n} \sum_l \sum_m s(k_{xl},y) b(k_{xl},x_u)$$

$$= \frac{1}{n} \sum_l \sum_m \rho(x_m,y) a(k_{xl},x_m) b(k_{xl},x_u),$$

where the matrix A describes the non-uniformity and can be calculated or determined experimentally. When the matrix $B = A^{-1}$, the estimated and actual data match. In one embodiment, the generalized transform algorithm is determined by inverting the matrix A and operating on a data matrix therewith.

19 Claims, 2 Drawing Figures

GENERALIZED RECONSTRUCTION TECHNIQUE

This application is a continuation-in-part of application Ser. No. 731,509 filed May 7, 1985, now pending.

BACKGROUND OF THE INVENTION

The present invention pertains to the art of data processing and image reconstruction. It finds particular application in the reconstruction of magnetic resonance images and will be described with particular reference thereto. However, it is to be appreciated that the invention is also applicable to other imaging modalities including geophysics, land sat, computerized tomography, digital x-ray, optics, ultrasonics, and the like.

Heretofore, magnetic resonance imaging has been conducted in the presence of a strong magnetic field. An object to be imaged was positioned in an image region with the strong magnetic field passing substantially uniformly therethrough. Magnetic dipoles of nuclei disposed within the imaging region tended to align with the strong magnetic field. Resonance excitation radio frequency pulses were applied to the image region to cause the magnetic dipoles to precess about the strong magnetic field. As magnetic dipoles precessed, corresponding radio frequency resonance signals were generated thereby. Gradient magnetic fields were applied transverse to the main magnetic field to encode the frequency and phase of the radio frequency resonance signals in accordance with the spatial position of the precessing magnetic dipole which generated each resonance signal component. Various techniques, which are well known in the art, may be implemented to excite resonance and spatially encode the resonance signals.

In the spin-echo technique, the excitation pulses were cyclically applied and the magnetic dipoles were permitted to precess or undergo free induction decay therebetween. Square gradient pulses were applied such that the resonance signals were frequency encoded along one axis and phase encoded along an orthogonal axis. Resonance signal data was collected with uniform sampling in time to form views comprised of discrete electronic data lines. In this manner, data space was covered on a uniform grid. Each collected data line was operated upon by a two dimensional fast Fourier transform matrix to transform or map the data from the frequency domain to the spatial domain or image space. Commonly, numerous views were collected to extract information on spin density and relaxation times with high resolution and accuracy. Other reconstruction techniques such as hybrid imaging, echo planer imaging, and concentric circle imaging have also been used and are applicable to the present invention.

In order to reconstruct an accurate and precise image representation, it was necessary that the frequency domain data be uniform. Non-uniformities, errors, or distortions of the coverage in the data space introduced aliasing and other errors in the image representation. In particular, a Fourier transform assumes or treats input data as being uniformly sampled. Any non-uniformity in the sampling causes errors in the resultant image representation.

Heretofore, it was necessary to provide uniformly sampled data for the Fourier transform step. This necessitated accurate and precise linearity in the main magnetic field and the gradient magnetic fields. The systems were designed to limit other deviations such as eddy currents, motion, field inhomogeneities, non-uniform sampling, phase errors, gradient errors, and the like which also caused errors and aliasing.

In accordance with the present invention, an apparatus and method are provided for transforming non-uniform input data into a uniform image representation, when changes in time sampling which lead to uniform data space coverage can not be implemented.

SUMMARY OF THE INVENTION

In accordance with one aspect of the present invention, a method of data processing is provided. Input data is discretely sampled in a first space or domain over an integral number of non-uniform points. The non-uniform sampled data is directly transformed from the first space into uniformly spaced, discrete points in a second space. More specifically to the preferred embodiment, the first space is an image space in which data is frequency encoded or the like. The second space is an image space with the discrete points arranged in a preselected spatial coordinate system, which may be selected to be non-uniform.

In accordance with another aspect of the present invention, data is collected which has spatial position and density information sampled non-uniformly therein. The collected data is operated upon with a generalized transform which transforms the non-uniformly sampled data directly, without interpolation into a selected, e.g. uniform, representation of spatial position and density.

In one embodiment, the generalized transform is iteratively improved. The spatial position and density information is encoded from a phantom having a known array of magnetic dipoles. In each iteration, the transformed representation of spatial position and density is compared with the known dipole array of the phantom to determine any discrepancy therebetween. The generalized transform is adjusted to reduce the discrepancy which corrects for motion and other underlying causes of the discrepancy.

In accordance with a more limited aspect of the present invention, a method of magnetic resonance imaging is provided. A main magnetic field is generated through an image region such that magnetic dipoles tend to align with the main magnetic field. Precession of the magnetic dipoles about the main magnetic field is cyclically excited such that each precessing magnetic dipole generates a radio frequency resonance signal component. Magnetic field gradients are caused across the main magnetic field to vary a phase and frequency of the resonance signal components, each generally in accordance with a spatial position of the generating magnetic dipole. The relationship between the phase, frequency, and spatial position of the precessing dipoles being non-uniform such that Fourier transforming the resonance signal components into real space would produce a distorted or blurred image representation. The resonance signal components are operated upon with a generalized transform which concurrently corrects for the non-uniformity between the phase, frequency, and spatial position and transforms the resonance signal components into a desired representation of the spatial position and density of the precessing magnetic dipoles.

In accordance with another aspect of the present invention, a data processing apparatus maps non-uniform data from a first space or domain uniformly or otherwise into a second space or domain. A sampling means discretely samples non-uniform first domain data.

A transform means operates on the non-uniform first domain data with a generalized transform algorithm which transforms or maps the non-uniform first domain data directly into uniformly or otherwise distributed second domain data.

In accordance with a more limited aspect, a magnetic resonance imaging apparatus is provided. A main magnetic field generating means generates a strong, main magnetic field through an image region such that magnetic dipoles disposed therein tend to align with the main magnetic field. An excitation means excites precession of the aligned magnetic dipoles such that the precessing dipoles generate radio frequency resonance signal components. A gradient field means causes magnetic field gradients which vary at least one of the phase and frequency of the resonance signal components in accordance with the spatial positions of the corresponding precessing magnetic dipoles. A sampling means discretely samples an integral number of data points of resonance signal components which are received by a radio frequency receiver. The sampled data points have frequencies or phases which are non-uniformly encoded with regard to the spatial position of the corresponding precessing magnetic dipoles. That is, the sampled data is non-uniform in the frequency domain. A transform means maps or transforms the non-uniformly sampled frequency domain data uniformly or otherwise into a spatial domain. A display means produces a man-readable display representing position and density of the precessing dipoles from the spatial domain data. Optionally, relaxation time parameters may also be represented.

A first advantage of the present invention is that it reduces and eliminates aliasing errors and other image degradation.

Another advantage of the present invention is that it enables motion artifacts to be removed and moving regions to be imaged.

Another advantage resides in a compensation for incorrect sampling in data space whether due to motion, eddy currents, poor timing, or the like.

Yet another advantage of the present invention is that hybrid and other image reconstruction techniques which utilize non-uniform data sampling are facilitated.

Still further advantages of the present invention will become apparent to those of ordinary skill in the art upon reading and understanding the following detailed description of the preferred embodiment.

BRIEF DESCRIPTION OF THE DRAWINGS

The invention may take form in various steps and arrangements of steps or in various parts and arrangements of parts. The drawings are only for purposes of illustrating a preferred embodiment of the invention and are not to be construed as limiting it.

DETAILED DESCRIPTION OF THE PREFERRED EMBODIMENTS

Figure 1:
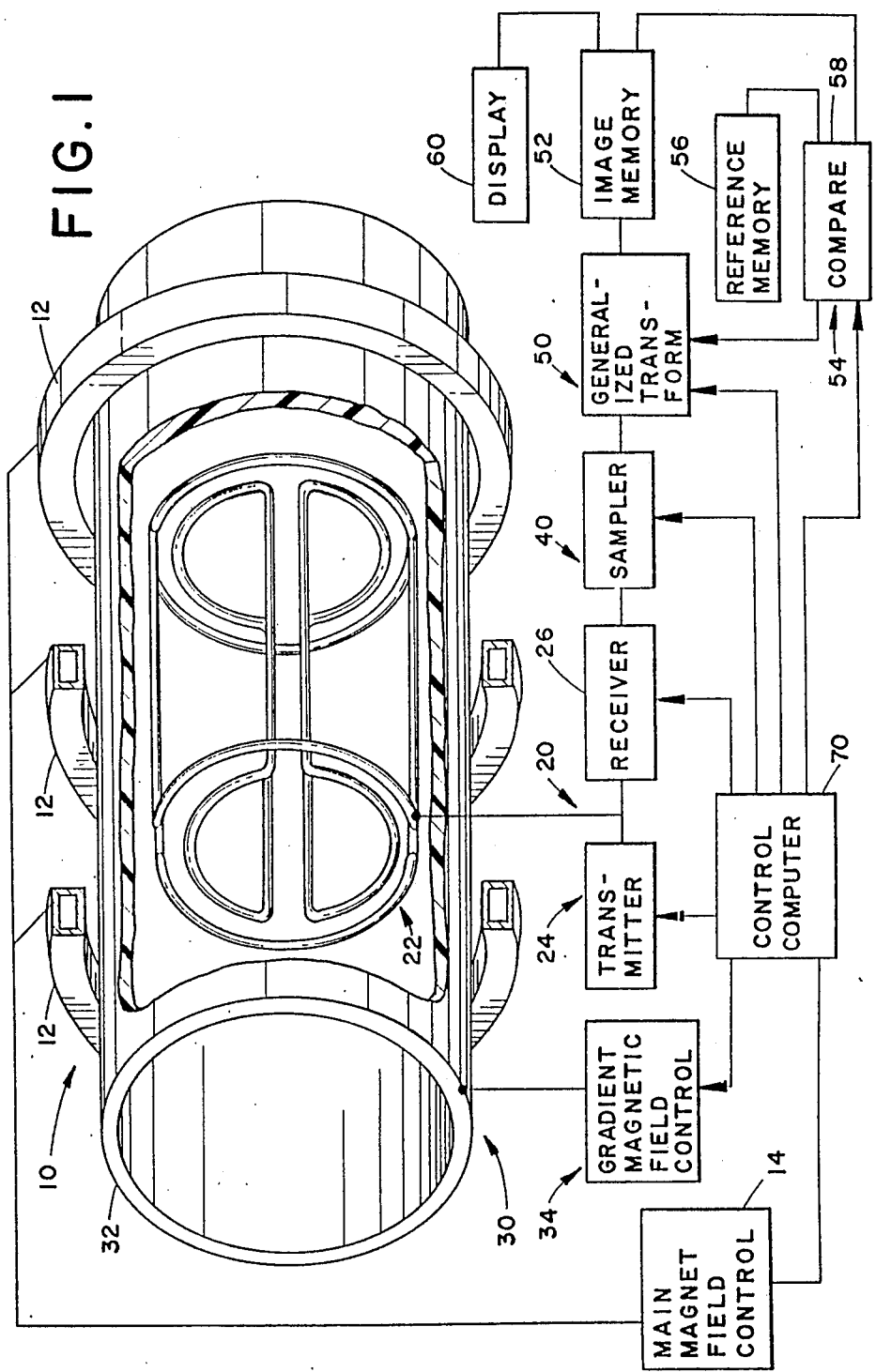
FIG. 1 is a diagramatic illustration of a magnetic resonance imaging apparatus in accordance with the present invention; and, FIG. 2 illustrates a series of components in conjunction with the derivation of a suitable generalized transform.

With reference to FIG. 1, a main magnetic field generating means 10 generates a strong, main magnetic field which extends generally linearly through an image region. A resonance excitation means 20 selectively excites precession of magnetic dipoles of nuclei in the image region about the main magnetic field. Each precessing magnetic dipole generates a component of a resonance signal. A gradient field means 30 selectively causes gradients across the main magnetic field in the image region at selectable orientations. The gradient magnetic fields spatially encode the resonance signal components transmitted by resonating magnetic dipoles within the image region. Specific to the preferred embodiment, square gradient field pulses encode the frequency and relative phase of each component in accordance with the spatial location of the corresponding generating dipole.

A sampling means 40 discretely samples an integral number of data points of the received resonance signal. The sampled data points are non-uniform in data space whether due to non-ideal gradients, phase encoding errors, non-uniform sampling, motion, or the like. A generalized transform means 50 transforms or maps the non-uniform sampled resonance signal data points from data space or the frequency domain to image space or spatial domain. The generalized transform, as described in greater detail herein below, concurrently corrects for the non-uniformities in the data space during the transformation of the data uniformly into image space. Optionally, the data may be transformed with a preselected non-uniformity which enhances a selected characteristic. A display means 60 provides a man-readable display of the image space data. In the preferred embodiment, the display provides an indication of the spatial position and density of the precessing magnetic dipoles. Other information such as relaxation times, chemical composition, bonding, the physical state of nuclei whose dipoles are precessing, and the like may also be extracted from the resonance signals. A computer controls means 70 controls and coordinates operation of the magnetic field and gradient control means, the resonance excitation means, the sampling and transform means, and the display means. In the preferred embodiment significant portions of all of these means are incorporated in the software of a common computer.

The main magnetic field means 10 includes a plurality of annular superconducting magnetics or fluid cooled, high power magnetics 12 for generating the main magnetic field generally axially therethrough. A main magnetic field control circuit 14 controls and applies appropriate electric power to the annular magnetics such that a substantially uniform and constant magnetic field is generated longitudinally therethrough.

The excitation means 20, in the preferred embodiment, includes a quadrature coil 22 which is connected with a radio frequency transmitter 24 for broadcasting radio frequency excitation pulses. The radio frequency pulses are of the appropriate timing and duration, as is known in the art, to cause precession of the magnetic dipoles about the main magnetic field. The quadrature coil 22 functions between excitation pulses as an antenna for a radio frequency receiver 26. The receiver 26 receives the analog resonance signal which includes a large multiplicity of superimposed resonance signal components. The frequency and relative phase of the components are indicative of the encoded spatial position of each generating nucleus.

The gradient field means 30 includes gradient field coils 32 which surround the imaged region for selectively applying gradient magnetic fields transversely across the main magnetic field. A gradient magnetic field control circuit 34 controls the angular orientation with which gradient fields are applied and the relative timing between the application of orthogonal gradient field pulses to control and select a phase encoding of the frequency of the resonance signal components. The exact sequence and timing between resonance exciting transmission and application of the gradient fields will vary in accordance with the imaging modality selected. Although the preferred embodiment is described in conjunction with spin-echo two dimensional Fourier transform imaging, it is to be appreciated that the apparatus and method are equally applicable to hybrid imaging, echo planer imaging, concentric circle imaging, and other imaging modalities.

The sampling means 40 discretely samples the received analog resonance signal. More specifically to the preferred embodiment, after each change in the gradient magnetic field, the received analog resonant signal is sampled again. Preferably, 2N views or samplings, each with a different application of the gradients, are collected per image. Within each view, an integral number of data points, preferably 2N points, of the received resonance signal are sampled. The sampling produces a series of one dimensional data lines of discrete, sampled values. It is to be appreciated that the sampling need not be uniform. Specifically, time intervals between the sampling of successive data points within a single data line may be varied, e.g. sinusoidally. Analogously, other non-uniformities in the sampling frequency, in the gradient fields, or the like may be applied as is appropriate to the imaging technique selected. For example, sinusoidally varying gradients may improve image quality in regions with motion of the same periodicity, e.g. cardiac, pulmonary, or the like.

In the preferred embodiment, the generalized transform means 50 transforms the frequency and phase encoded data lines from the frequency domain to the image space or the spatial domain. As explained in more detail in the following derivation and examples, the generalized transform in a single operation (1) corrects for the non-uniformity in data space and (2) transforms the sampled data from data space to image space. As each data line is transformed, it is added to the data stored in an image memory 52. The compilation of the transformed data lines of the 2N views produces an electronic representation of an image of the spatial position and density of the resonating nuclei.

The generalized transform is selected or adjusted specifically for the non-uniformity(s) which are present in a specified system or intended application. For predictable or calculatable non-uniformities, the generalized transform may be calculated from a conventional Fourier transform and an equation which describes the non-uniformity. The generalized transform for non-uniform sampling and eddy currents is particularly amenable to calculation. For other non-uniformities, such as motion, it may be advantageous to determine the generalized transform empirically. The calculated generalized transforms are fine tuned or rendered more accurate by iterative adjustment. To this end, the apparatus includes a means 54 for iteratively adjusting the transform. In the illustrated embodiment, a reference memory 56 stores a representation of the image space data which would be generated if the image reconstruction were defect free. A comparing means 58 compares the reference representation with the actual image representation compiled in the image memory 52 to determine the deviations therebetween. For example, a phantom having a regular rectangular array of elements may be disposed in the image region and a representation of the same rectangular coordinate array may be stored in reference memory 56. The comparing means may then compare the position of the elements from the image memory 52 and from the reference memory 56 to determine the deviation or shift therebetween, aliasing, or the like. The comparing means may then adjust the generalized transform in accordance with the principles set forth below to reduce the deviation between the reference and the reconstructed image data. This process is iteratively repeated causing the generalized transform to correct for the non-uniformity progressively more accurately. As explained below, other iterative adjustments may be made to correct for other non-uniformities in the received data.

When the data space is non-uniformly covered, for whatever reasons, the reconstructed image will suffer accordingly. In the past, one procedure for improving the image was to interpolate the data to approximate a correction for the non-uniformity. However, this filtering of data led to an incomplete recovery of missing frequency information or other data.

The generalized transform, which is a brute force, finite discrete transform procedure, transforms the non-uniform data directly without interpolation or approximation. In the two dimensional Fourier transform method, the input data g(f) is discretely sampled over n points. The signal G(t) is also discretely sampled by the sampling means 40 over n points. Preferably, the sampling is uniform in time such that the orthogonal functions are simple trigonometric functions to simplify the calculations. That is, for uniform sampling in time:

$$G(t) = \sum_{K=-N}^{N-1} g(f_k) \exp(-i2\pi f_k t) \tag{1}$$

$$\hat{g}(f_m) = \frac{1}{n} \sum_{l=-N}^{N-1} G(t_l) \exp(i2\pi f_m t_l), \tag{2}$$

where $\hat{g}$ is the estimate of the image.

It is to be appreciated that fast inversion methods, such as fast Fourier transforms, may be utilized rather than these standard forms for discrete Fourier transforms. When using two dimensional Fourier transform reconstruction methods, uniform square grid coverage is ideal. When using projection reconstruction techniques, uniform radial coverage of data space is preferred.

Substituting Equation (1) into Equation (2), the estimated transform function, $\hat{g}(f_m)$, may be expressed as:

$$\hat{g}(f_m) = \frac{1}{n} \sum_{l=-N}^{N-1} \sum_{k=-N}^{N-1} g(f_k) \exp(i2\pi t_l(f_k - f_m)) \tag{3a}$$

$$= \sum_{k=-N}^{N-1} g(f_k) \frac{1}{n} \sum_{l=-N}^{N-1} \exp(-i2\pi t_l(f_k - f_m)). \tag{3b}$$

The estimated transform function may be expressed in terms of a point spread function, h, which in the present example, represents discrete points inverted with a discrete function. That is:

$$\hat{g}(f_m) = \sum_{k=-N}^{N-1} g(f_k) h_{km} \tag{3c}$$

Of course, when a perfect uniformly sampled match is desired, $h_{km} = \delta_{km}$ where $\delta$ is the Kronecker delta function and so $$\hat{g}(f_m) = g(f_m) \tag{3d}$$

Note a uniform sampled match need not be the desired result and the method still applies. Specifically, the $f_m$ values may be non-uniformly spaced as in the case of a non-linear gradient or inhomogeneous static field.

When there is a non-ideal coverage of data space in which the uniformly sampled phases may assume numerous values, the signal may be expressed by the equation:

$$G(t) = \sum_k g(f_k) a(f_k, t) \tag{4a}$$

Here $a(f,t)$ are elements of a matrix A which describes the non-ideal coverage. In the ideal case $$a(f_k, t) = e^{-i2\pi f_k t} \tag{4b}$$

The phase will be non-uniform when t is non-uniformly sampled. Other distortions occur when eddy currents are present. Flow and other motion can likewise cause problems because the phase becomes $2\pi f_k(t)t$. However, as is shown below, the present invention can account for all these effects.

The estimated transform may be expressed in terms of the elements of a matrix B as:

$$\hat{g}(f_m) = \frac{1}{n} \sum_l G(t_l) b(f_m, t_l). \tag{5}$$

Making the same substitutions as in Equations (3a) and (3b), $$\hat{g}(f_m) = \frac{1}{n} \sum_l \sum_k g(f_k) b(f_m, t_l) a(f_k, t_l) \tag{6a}$$

$$= \sum_k g(f_k) \frac{1}{n} \sum_l b(f_m, t_l) a(f_k, t_l). \tag{6b}$$

Comparing Equations (3c) and (6b), the estimated image function $\hat{g}(f_m)$ and the actual image function $g(f_k)$ will be identical when:

$$\frac{1}{n} \sum_l b(f_m, t_l) a(f_k, t_l) = \delta_{km}. \tag{7}$$

Equivalently in matrix notation:

$$BA = I \tag{8a}$$

where:

$$(B)_{ml} = \frac{1}{n} b(f_m, t_l) \tag{8b}$$

$$(A)_{lk} = a(f_k, t_l). \tag{8c}$$

Solving Equation (8a), the matrix B is defined as:

$$B = A^{-1} \tag{9}$$

The matrix B is defined when the determinant of A, $|A|$, is non-zero or A is non-singular.

By way of example, in magnetic resonance imaging, the frequency f is equal to $\gamma \vec{G} \cdot \vec{r}$, where $\gamma$ is the gyromagnetic ratio and $\vec{r}$ is the position of the nucleus relative to the gradient field. The phase at a coordinate position (k, l) may be represented by the equation:

$$f_{k,l} t(l) = \int_{-T}^{t(l)} \vec{G}(r_k) \cdot \vec{r_k}(t) dt + \text{a dephase portion}, \tag{10}$$

where t(l) is a function of l. The dephase portion is on prior to sampling. For one sided sampling, such as in a free induction decay experiment, the dephase portion may be zero. For spin-echo or field echo data, the dephase portion is ideally $-\gamma \vec{G} \cdot \vec{r} t$ so that the echo occurs at $t=0$. Otherwise, the dephase portion is also an integral over $\vec{G}(t) \cdot \vec{r}(t)$ which can at most add a position dependent phase error. This poses no constraints on the present technique and can, in fact, be accounted for as shown in Equation (11) and the following discussion.

As another example, the non-uniformity in sampling due to motion is caused by $\vec{G} \cdot \int \vec{r}(t) dt$ not being linear and can also be accounted for. From Equations (3a) and (4a), the matrix A may be represented as:

$$a(f_k, t_l) = \exp(i 2\pi f_k t(l)) \tag{11}$$

The $|A|$ is zero if two rows are equal. Two rows are equal when the same view is repeated or if the frequency varies with position such that:

$$f_{k,l} t(l) = f_{k,l'} t(l') \tag{12a}$$

for all k and $l \neq l'$.

As a specific case for motion, consider a body which is at rest from $-n\Delta x$ to zero and expands linearly from zero to $(n-1)\Delta x$. The matrix A then becomes $$a(x_k, f_x) = e^{-i2\pi x_k f_x} \tag{12b}$$

for $-n\Delta x \leq x \leq 0$ and $$a(x_n, f_x) = e^{-i2\pi x k(1 + \alpha(f_x)/(n-1)\Delta x} \tag{12c}$$

for $0 < x \leq (n-1)\Delta x$, where $\alpha(f_x)$ is the amplitude of the motion at $x_{n-1}$ for the $f_x$'th sampled point. We have used the canonical variables $x, f_x$ rather than $f, t$ to relate to the physical nature of this problem. Here $|A|$ is non-zero as required and so the motion can be corrected for.

As another example, the effects of field inhomogenity phases can be removed if the inhomogenities are known prior to the reconstruction. Phase shifts due to poor choice of peak positioning can likewise be removed. Analogously, motion can be corrected if a model exists for the motion. This can be extended to higher dimensions to correct for other errors such as phase shifts due to changing eddy currents or relaxation time effects in finite sampling or more complicated motion problems. However, rather than inverting a matrix, a tensor of rank 2n, where n is the dimension being considered, must be inverted.

When correcting for motion, each patient will have a different pattern and a new matrix must be derived and inverted for each scan. For other non-uniformities, such as non-uniform sampling of the data with the same non-uniformity in each scan, the matrix inverse may be stored in a look-up table.

As another example, data is sampled non-uniformly in the hybrid technique of the above referenced patent application. Here, n points are non-uniformly sampled and the sampling pattern is periodically nested in the data. The mth point in the periodically repeating subset is shifted by $a_m$ from the 0th point in a uniform sampling grid, where m is greater than 0 and less than $n-1$. For example, if $a=m\Delta t$, then the sampling is uniform and no aliasing occurs. When $a_m \neq m\Delta t$, then the sampling is non-uniform in time and aliasing will occur if a conventional inverse Fourier transform is applied. The non-uniform sampling in time creates superimposed or aliased images, $g(f - lf_{Nyq})$ where l is greater than $-(n-1)$ and less than $(n-1)$ and $f_{Nyq}$ is the Nyquist frequency $1/(2\Delta t)$. The n superimposed or aliased images may be resolved by breaking the data up into n data sets, each of the same length as the acquired data, 2N. The mth set of data is of the form:

$$(\ldots g_{m-n}, 0,0, \ldots 0, g_m, 0,0, \ldots 0, g_{m+n}, \ldots). \quad (13)$$

Under the sampling theorem, the discretely sampled input data, $g_s(t)$ can be expressed as:

$$g_s(t) = g(t) \sum_{j=-N}^{N-1} \delta(t - j\Delta t). \quad (14)$$

For $\Delta t' = n\Delta t$, the mth data set may be denoted:

$$g_{sm}(t) = g(t) \sum_{j=-N}^{N-1}{}^{*} \delta(t - ja_m\Delta t'/n), \quad (15)$$

where the star(*) indicates that every mth point is used and the limits are defined in accordance with the value of m. The Fourier transform of the non-uniformly sampled mth data set, $h_{mk}(f)$ is expressed as:

$$h_{mk}(f) = \sum_{l=1-k}^{n-k} g(f + 2lf_N/n)e^{i2\pi la_m/n}, \quad (16)$$

where:

$$f_N(1-2k/n) < f < f_N(1-2(k-1)/n) \quad (17a)$$

for $$1 \leq k \leq n \quad (17b).$$

That is, the frequency is restricted to divisions of the Nyquist frequency. For each frequency shift, it is to be appreciated, the Fourier transform is recalculated.

It will be noted that an overlap occurs for the band-limited function n times in each of the intervals of Equation (17a). The shift theorem which has been used to obtain the phase term in Equation (16) assumes shifts to the right, along a positive t axis. For example, with $k=1$ and $n=4$, $$h_{ml} = \sum_{l=0}^{3} g_l e^{i\pi la_m/2}. \quad (18)$$

Note that the superimposed images $g_l$ create an aliasing problem. For an artifact free (un-aliased) image, only $g_o$ is desired.

In vector and matrix notation, Equation (18) may be written as (with H and G vectors and A a matrix):

$$H_k = A_k G_k \quad (19a),$$

where $$(H_k)_m = h_{mk} \quad (19b)$$

$$(G_k)_l = g_l \quad (19c)$$

$$(A_k)_{lm} = \exp(i2\pi la_m/n) \quad (19d),$$

where $1-k \leq l \leq n-k$ and $1 \leq k \leq n$. The single, non-aliased image $(G_k)$ is again the inverse of the matrix A multiplied by the Fourier matrix $H_k$, i.e.:

$$G_k = A_k^{-1} H_k \quad (20).$$

By way of a specific example, $a_m = ma$, $n=4$, and m may assume the four values 0, 1, 2, and 3. In this example, the specific values of the Fourier transform matrix, according to the formula of Equation (16), with the actual data removed, i.e., the ratio of h/g of the specific example, is given by the following table:

| h/g | g$_{-3}$ | g$_{-2}$ | g$_{-1}$ | g$_0$ | g$_1$ | g$_2$ | g$_3$ |
|---|---|---|---|---|---|---|---|
| h$_0$ | 1 | 1 | 1 | 1 | 1 | 1 | 1 |
| h$_1$ | $e^{-i3\pi a/2}$ | $e^{-i\pi a}$ | $e^{-i\pi a/2}$ | 1 | $e^{i\pi a/2}$ | $e^{i\pi a}$ | $e^{i3\pi a/2}$ |
| h$_2$ | $e^{-i3\pi a}$ | $e^{-i2\pi a}$ | $e^{-i\pi a}$ | 1 | $e^{i\pi a}$ | $e^{i2\pi a}$ | $e^{i3\pi a}$ |
| h$_3$ | $e^{-i9\pi a/2}$ | $e^{-i3\pi a}$ | $e^{-i3\pi a/2}$ | 1 | $e^{i3\pi a/2}$ | $e^{i3\pi a}$ | $e^{i9\pi a/2}$ |

It is to be noted that the elements on the right side of the table for $G_l$ are complex conjugates of those on the left for the same absolute value of l this simplifies computer storage of these correction factors.

Figure 2:
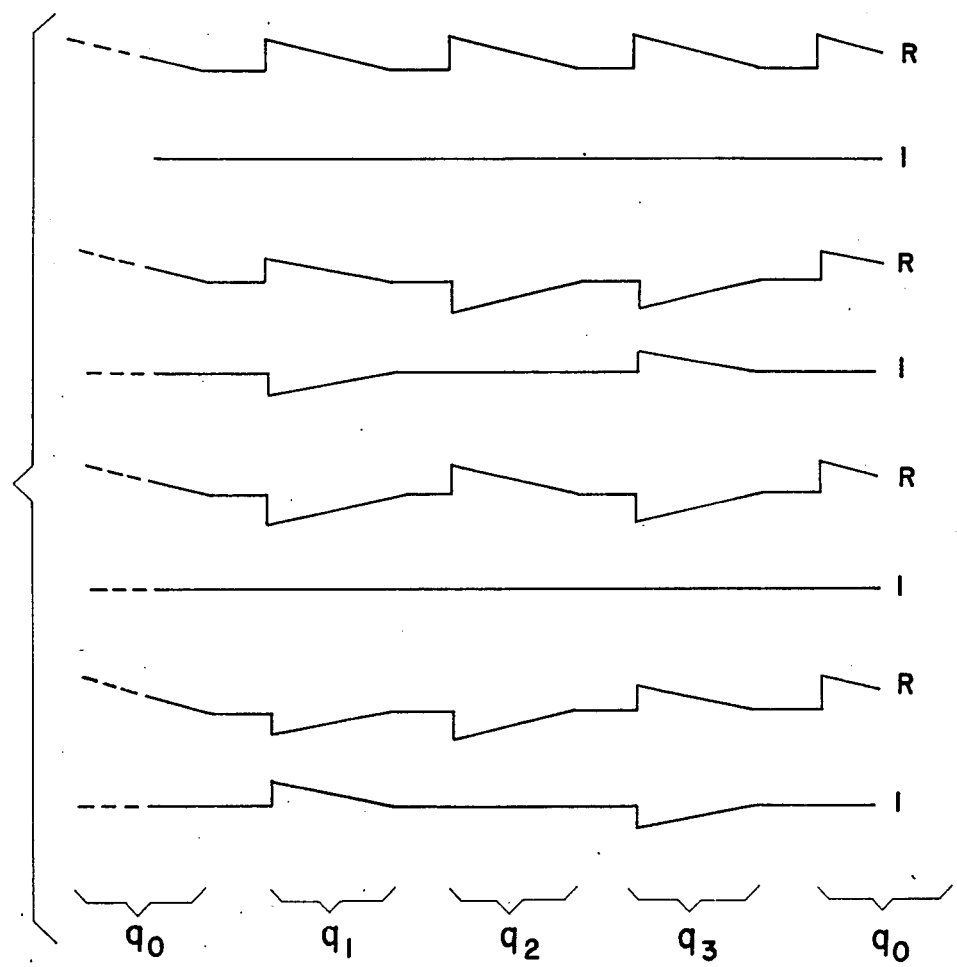

It is to be noted that when $a=1$, each of the columns adds to zero except for the $g_o$ column which sums to 4. This is illustrated pictorially in FIG. 2 which illustrates columns $g_o$ through $g_3$. The values of $g_o$ for each value of k are calculated by inverting the matrix equation in accordance with Equation (20). Often, the assumed position of the shifted points in data space is at the expected grid point. This leads to a phase shifted estimate for $h_k$ which may be designated as $\bar{h}_k$. The corrected value is then $$h_k(f) = e^{i\pi l\delta k/N} \bar{h}_k(f) \quad (21),$$

where $\delta_k = a_k - k$. The value of the $\delta_k$ may be derived if the equation of the non-uniformity is known, may be determined experimentally, or may be determined by trial and error. That is, the value of $\delta$ is iteratively increased or decreased until the error is minimized. Applying Equation (20), the value of $g_o(f)$ is recovered.

It is to be appreciated that the application may be extended to more than two dimensions. For an n-fold repetition of $n_1 \times n_2$, the zero filling is done on each two dimensional Fourier transform image with a total of $n_1 n_2$ such images. With $n_1 = n_2 = n_3$ the two dimensional equivalent to Eq(1b) becomes $$h_{mm'k}(x,y) = \quad (22)$$

$$\sum_{l_x(k)} \sum_{l_y(k)} g(x - l_x x_N, y - l_y y_N) \exp(i2\pi(l_x a_{xm} + l_y a_{ym'})/n)$$

where k refers to one of the $n^2$ regions in which (x,y) lie.

As another example, a conventional spin-echo sequence is applied to the image region. The gradient is applied as square pulses, although eddy currents and field inhomogeneities may distort the gradients or cause phase errors. For these and the other reasons set forth above, the data may be sampled non-uniformly. For a given y, the estimated spin density, $\hat{\rho}(x,y)$, is related to the sampled resonance signal, $s(k,y)$ as:

$$\hat{\rho}(x,y) = \frac{1}{n} \sum_{l=-N}^{N} s(k_{x,l},y) b(k_{x,l},x). \tag{23}$$

The matrix B including the matrix elements $b(k,x)$ describes the relationship between the actually sampled data and the data that would have been sampled from a uniform system. Conversely, $$s(k_x,y) = \sum_{m=-n}^{N-1} \rho(x_m,y) a(k_x,x_m), \tag{24a}$$

where in accordance with the previous discussion, $$a(k_x,x_m) = e^{-ik_x x_m} \tag{24b}$$

As discussed above, the matrix A which describes the non-uniformity can be calculated or determined by trial and error. Again, the estimated spin density $\hat{\rho}(x,y)$ is related to the actual spin density $\rho(x,y)$ by:

$$\hat{\rho}(x_u,y) = \frac{1}{n} \sum_{l=-N}^{N-1} \sum_{m=-N}^{N-1} \rho(x_m,y) a(k_{x,l},x_m) b(k_{x,l},x_u). \tag{25}$$

The removal of the effects of local field inhomogeneities on the image is another correction which can be made using the present invention. The generalized transform can handle the local phase problems and allow imaging in half the normal time by using only one half of the sampled data. Without the following technique, the images would be shaded and of little value.

In a two dimensional system, extending the A and B matrixes in both the x and y directions, the signal can be described as:

$$s(k_x,k_y) = \sum_{l,m} a(k_x,l) a_2(k_y,m) e^{i\phi(l,m)} \rho(x_l,y_m) \tag{26}$$

for the case where $k_x \geq 0$. The symmetrized data for the case of $k_x < 0$ is determined from the case of $k_x \geq 0$ data, i.e.:

$$s(-k_x,k_y) = s^*(k_x,-k_y) \tag{27a}$$

Substituting from Equation (26):

$$s(-k_x,k_y) = \sum_{l,m} a_1^*(k_x,l) a_2^*(-k_y,m) e^{-i\phi(l,m)} \rho(x_l,y_m) \tag{27b}$$

which can also be written:

$$s(-k_x,k_y) = \sum_{l,m} a_1(-k_x,l) a_2(k_y,m) f(k_x,l,m) \rho(x_l,y_m). \tag{27c}$$

for all $k_x$, where:

$$f(k_x,l,m) = e^{-i\alpha(k_x)\phi(l,m)} \tag{28a}$$

$$\alpha(k_x) = 1 \text{ for } k_x > 0 \tag{28b}$$

$$\alpha(k_x) = -1 \text{ for } k \leq 0 \tag{28c}$$

Taking the inverse transforms in x and y, the estimated spin density may be defined as:

$$\hat{\rho}(x_{l'},y_{m'}) = \sum_{p} b_1(k_{x,p},l') a_1(k_{x,p},l,m') \rho(x_l,y_{m'}). \tag{29}$$

where the estimated and actual spin densities are related by $$\hat{\rho}(x_{l'},y_{m'}) = \rho(x_{l'},y_m) e^{i\phi(l',m')} \tag{30}$$

The solution is then obtained from:

$$\sum_{p,l} b_1(k_{x,p},l') a_1(k_{x,p},l) f(k_{x,p},l,m') = \delta_{ll'} e^{i\phi(l',m')}. \tag{31}$$

Defining the matrixes C, B, and A $$(C)_{l'l'} = e^{i\phi(l',m')} \tag{32a}$$

$$(B_1)_{l'p} = b_1(k_{x,p},l') \tag{32b}$$

$$(A_1)_{pl} = a_1(k_{x,p},l) f(k_{x,p},l,m') \tag{32c}$$

then these matrices are related by $$B_1 = C(A_1)^{-1} \tag{33}$$

Because $B_1$ depends on $m'$, n different matrix inversions may be required.

In this manner, the symmetry of the collected magnetic resonance data may be utilized to replace or correct deficient portions of the collected data. Further, image reconstruction time may be halved. Thus, using a generalized matrix inversion, one can correct for non-uniform coverage in data space whether attributable to non-uniform sampling in time, gradient shaping problems, motion, or local phase aberrations. In many instances, only a single matrix need be inverted and may be stored in a table.

The invention has been described with reference to the preferred embodiment. Obviously, modifications and alterations will occur to others skilled in the art. It is intended that the invention be construed as including all such alterations and modifications in so far as they come within the scope of the appended claims or the equivalents thereof.

Having thus described the preferred embodiment, the invention is now claimed to be:

1. A method of magnetic resonance imaging comprising:

generating a main magnetic field through an image region which tends to align magnetic dipoles of nuclei to be imaged therewith;

cyclically exciting precession of the magnetic dipoles of the imaged nuclei about the main magnetic field, each nuclei generating radio frequency components of a resonance signal as dipole precession decays toward alignment with the main magnetic field;

causing magnetic field gradients across the main magnetic field to vary a phase and frequency of resonance signal components generally in accordance with a spatial position of the generating nuclei, the relationship between the spatial position and at least one of the phase and frequency being non-uniform such that Fourier transforming the resonance signal into real space would produce a distorted image representation;

operating on the resonance signal with a generalized transform which concurrently (1) corrects for the non-uniformity between the spatial position and at least one of the phase and frequency and (2) transforms the resonance signal into a respresentation of the spatial position and density of the imaged nuclei.

2. A method of magnetic resonance imaging comprising:

generating a main magnetic field through an image region which tends to align magnetic dipoles of nuclei to be imaged therewith;

positioning reference nuclei with preselected densities in preselected spatial positions in the image region and a subject in the image region;

cyclically exciting precession of the magnetic dipoles of the subject and reference nuclei about the main magnetic field, each nuclei generating radio frequency components of a resonance signal as dipole precession decays toward alignment with the main magnetic field;

causing magnetic field gradients across the main magnetic field to vary a phase and frequency of resonance signal components generally in accordance with a spatial position of the generating nuclei, the relationship between the spatial position and at least one of the phase and frequency being non-uniform whereby Fourier transforming the resonance signal into real space would produce a distorted image representation;

operating on the resonance signal with a generalized transform which concurrently (1) corrects for the non-uniformity between the spatial position and at least one of the phase and frequency and (2) transforms the resonance signal into a representation of the spatial position and density of the subject and reference nuclei;

comparing the preselected spatial positions and densities of the reference nuclei with the representation to determine discrepancies therebetween;

adjusting the generalized transform to decrease the discrepancies;

repeating at least the operating step with the adjusted generalized transform to produce an improved representation of at least the subject nuclei.

3. The method as set forth in claim 2 wherein the preselected spatial positions are arranged in a preselected grid format.

4. A method of magnetic resonance imaging comprising:

generating a main magnetic field through an image region which tends to align magnetic dipoles of nuclei to be imaged therewith;

cyclically exciting precession of the magnetic dipoles of the subject and reference nuclei about the main magnetic field, each nuclei generating radio frequency components of a resonance signal as dipole precession decays toward alignment with the main magnetic field;

causing magnetic field gradients across the main magnetic field to vary a phase and frequency of resonance signal components generally in accordance with a spatial position of the generating nuclei;

sampling the resonance signal non-unformly, which non-uniform sampling causes a non-uniformity in relationships between the spatial position and at least one of the phase and frequency whereby Fourier transforming the non-uniform resonance signal samplings into real space would produce a distorted image representation; and, operating on the non-uniform resonance signal samplings with a generalized transform which concurrently (1) corrects for the non-uniformity between the spatial position and the at least one of the phase and frequency and (2) transforms the resonance signal sampling into a representation of the spatial position and density of the imaged nuclei.

5. A method of data processing comprising:

discretely sampling input data in a first space over n sampled points non-uniformly in time, where n is an integer; and, directly transforming the sampled data from the non-uniformly sampled points in the first space into preselected disposed points in a second space.

6. The method as set forth in claim 5 wherein the second space points are uniformly spaced.

7. The method as set forth in claim 5 wherein the first space is a spatial frequency domain and the second space is a spatial domain or any conjugate variable pair.

8. The method as set forth in claim 5 wherein the first space is a spatial domain and the second space is a time domain.

9. The method as set forth in claim 5 wherein the input data is frequency encoded in accordance with a rectangular coordinate system of the spatial domain.

10. The method as set forth in claim 9 wherein the input data includes radio frequency components generated by nuclei precessing about a first magnetic field.

11. The method as set forth in claim 10 further including the step of spatially encoding the frequency of the radio frequency components by causing magnetic field gradients across the first magnetic field.

12. The method as set forth in claim 11 wherein the step of spatially encoding the frequency includes phase encoding the radio frequency components.

13. The method as set forth in claim 5 further including, before the discrete sampling step, the step of collecting input data from a sample with a known spatial configuration; and, after the direct transforming step, comparing the data transferred into the second space with the known spatial configuration.

14. The method as set forth in claim 13 further including the step of modifying the transforming step to bring the data transformed into the second space and the known spatial configuration into greater conformity.

15. The method as set forth in claim 14 wherein the input data is sampled line by line, each line being transformed by being operated upon by a transform matrix.

16. A method of data processing comprising:

sampling reference data from a sample with a known configuration in a first space over non-uniformly sampled points;

transforming the sampled data from the non-uniformly sampled points in the first space into a second space with a first transform matrix;

comparing the reference data transformed into the second space with the known configuration;

producing a correction matrix which substantially converts the transform reference data into the known configuration;

operating on the first transform matrix with the correction matrix to produce a second tranform matrix;

discretely sampling input data from a subject in a first space over n non-uniformly sampled points, where n is an integer and, directly transforming the sampled input data from the non-uniformly sampled points in the first space into the second space with the second transform matrix.

17. The apparatus as set forth in claim 16 wherein the transform means operates on the sampled frequency domain data with a generalized transform which transforms non-uniformly sampled frequency domain data into the spatial domain.

18. A magnetic resonance imaging apparatus comprising:

a means for generating a main magnetic field through an image region, such that magnetic dipoles disposed in the image region tend to align with the main magnetic field;

an excitation means for exciting precession of the aligned magnetic dipoles about the main magnetic field such that the precessing magnetic dipoles generate radio frequency resonance signal components;

a gradient field means for causing magnetic field gradients to vary at least one of the phase and a frequency of the resonance signal components in accordance with spatial positions of the precessing magnetic dipoles;

a radio frequency receiver for receiving the resonance signal components;

a sampling means for discretely sampling an integral number of data points of the received resonance signal components, which sampled data points have frequencies which are non-uniform with regard to the spatial position of the precessing magnetic dipoles such that the sampled data is non-uniform in a frequency domain;

a transform means for mapping the non-uniformly sampled frequency domain data into a selected spatial domain with a generalized transfer function;

a comparing means for comparing the transformed spatial domain data from a preselected object in the image region with a preselected spatial domain configuration, the comparing means being operatively connected with the transform means to receive transformed spatial domain data therefrom; and, a transform modifying means for modifying the generalized transform function in accordance with the comparison between a representation of the display and the preselected spatial domain configuration to reduce any non-conformity therebetween; and, a display means for producing a man-readable display representing the uniform spatial domain data.

19. A data processing apparatus for mapping non-uniformly sampled data in a first space uniformly into a second space, the apparatus comprising:

a sampling means for discretely sampling non-uniform first space data;

a transform means for operating on the sampled first space data with a transform algorithm which transforms the non-uniformly sampled first space data directly into a second space data which has a preselected distribution; and, an iterative adjustment means for iteratively adjusting the transform algorithm to improve the quality of the distribution of the second space data.

* * * * *